United States Patent
Lukesch

(10) Patent No.: US 10,954,537 B2
(45) Date of Patent: Mar. 23, 2021

(54) AMINO ACIDS BEARING A NORBORNENE MOIETY

(71) Applicant: VALANX BIOTECH GMBH, Klosterneuburg (AT)

(72) Inventor: Michael Lukesch, Vienna (AT)

(73) Assignee: VALANX BIOTECH GMBH, Graz (AT)

( * ) Notice: Subject to any disclaimer, the term of this patent is extended or adjusted under 35 U.S.C. 154(b) by 0 days.

(21) Appl. No.: 16/631,928

(22) PCT Filed: Jul. 20, 2018

(86) PCT No.: PCT/EP2018/069726
§ 371 (c)(1),
(2) Date: Jan. 17, 2020

(87) PCT Pub. No.: WO2019/016354
PCT Pub. Date: Jan. 24, 2019

(65) Prior Publication Data
US 2020/0157586 A1    May 21, 2020

(30) Foreign Application Priority Data
Jul. 20, 2017    (EP) .................................... 17182393

(51) Int. Cl.
*C12P 13/04*    (2006.01)
*C07C 229/32*    (2006.01)
*C07C 323/55*    (2006.01)

(52) U.S. Cl.
CPC ............ *C12P 13/04* (2013.01); *C07C 229/32* (2013.01); *C07C 323/55* (2013.01); *C12Y 401/02005* (2013.01)

(58) Field of Classification Search
None
See application file for complete search history.

(56) References Cited

FOREIGN PATENT DOCUMENTS

WO    2013108044 A2    7/2013

OTHER PUBLICATIONS

Clerici, Francesca et al; "A highly diastereoselective synthesis of new polyhydroxy 2-aminonorbornanecarboxylic acids." J. Org. Chem. (2001) 66 p4941-4944.*
Jones et al., "The use or norbornene derivatives in the synthesis of conformationally constrained peptides and pseudo-peptides", Letters in Peptide Science, 1998, vol. 5, pp. 171-173.
Lang et al., "Genetically encoded norbornene directs site-specific cellular protein labelling via a rapid bioorthogonal reaction", Nature Chemistry, Feb. 2012, vol. 4, pp. 298-304.
Steinreiber et al., "Threonine aldolases—an emerging tool for organic synthesis", Therahedron, 2007, vol. 63, pp. 918-926.
International Search Report for PCT/EP18/69726 dated Oct. 8, 2018; 5 pages.
Written Opinion for PCT/EP18/69726 dated Oct. 8, 2018; 5 pages.
International Preliminary Report on Patentability for PCT/EP18/69726 dated Jan. 21, 2020; 6 pages.
Extended European Search Report for corresponding European Patent Application No. 171823933 dated Nov. 24, 2017; 6 pages.

* cited by examiner

*Primary Examiner* — Fred H Reynolds
(74) *Attorney, Agent, or Firm* — Loza & Loza, LLP; Michael F. Fedrick

(57) ABSTRACT

The invention relates to a novel amino acid having a norbornene group and polypeptide comprising the novel amino acid compounds. The invention also relates to a method of producing polypeptides comprising a norbornene group and to the use of said polypeptides.

14 Claims, 3 Drawing Sheets

AMINO ACIDS BEARING A NORBORNENE MOIETY

CROSS-REFERENCE TO RELATED APPLICATIONS

This application is the U.S. national stage of International Patent Application No. PCT/EP2018/069726, filed on Jul. 20, 2018 and entitled NOVEL AMINO ACIDS BEARING A NORBORNENE MOIETY, which claims the benefit of priority under 35 U.S.C. § 119 from European Patent Application No. 17182393.3, filed Jul. 20, 2017. The disclosures of the foregoing applications are incorporated herein by reference in their entirety.

FIELD OF THE INVENTION

The invention relates to novel amino acids bearing a norbornene moiety, to a process for the enzymatic preparation thereof and use of the novel compounds in click chemistry or site specific protein modification.

BACKGROUND ART

The selective modification of biological molecules is one option in modern drug development. Beta-hydroxy amino acids bearing a norbornene reactive group are notably useful as building blocks in peptide and protein chemistry as well as for synthons for active pharmaceutical ingredients. Current approaches for producing amino acids with said functionality use multiple synthetic steps in organic solvents with subsequent laborious work-up procedures (Lang et al., 2013).

WO2013/108044 discloses polypeptides comprising an amino acid having a norbornene group. Specifically, Nε-5-norbornene-2-yloxycarbonyl-L-lysine is genetically incorporated by using an orthogonal tRNA synthetase/tRNA pair.

There is still a need for novel amino acids bearing a norbornene group which may react with various chemical groups. Specifically for novel amino acids which react with very fast rates at physiological pH in aqueous conditions and at room temperature.

SUMMARY OF INVENTION

It is an object of the present invention to provide novel amino acids bearing a norbornene group. The object is solved by the subject matter of the present invention.

The present invention relates to novel amino acids bearing a norbornene group, to methods for producing said novel amino acids and to their use.

One embodiment of the invention relates to compounds of general formula I,

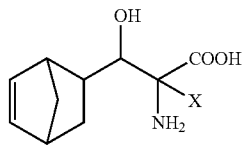

wherein X is a H or —$C_1$-$C_6$alkyl, optionally substituted by hydroxy, halogen, amine, thiol, or carboxy.

A further embodiment of the invention relates to a compound selected from the group consisting of D- or L-3-norbornene serine, D- or L-2-methyl alcohol-3-norbornene serine, D- or L-2-methyl-3-norbornene serine, D- or L-2-isopropyl alcohol-3-norbornene serine, D- or L-2-methyl thiol-3-norbornene serine, D- or L-2-butane amine-3-norbornene serine, D- or L-2-isopentane-3-norbornene serine, D- or L-2-butyric acid-3-norbornene serine, D- or L-2-methylpyrrolidine-3-norbornene serine, D- or L-2-methyl (propyl)sulfane-3-norbornene serine, D- or L-2-1-butylguanidine-3-norbornene serine, L-2-propionamide-3-norbornene serine, and L-2-butyramide-3-norbornene serine.

One embodiment of the invention relates to compound selected from Table 1.

TABLE 1

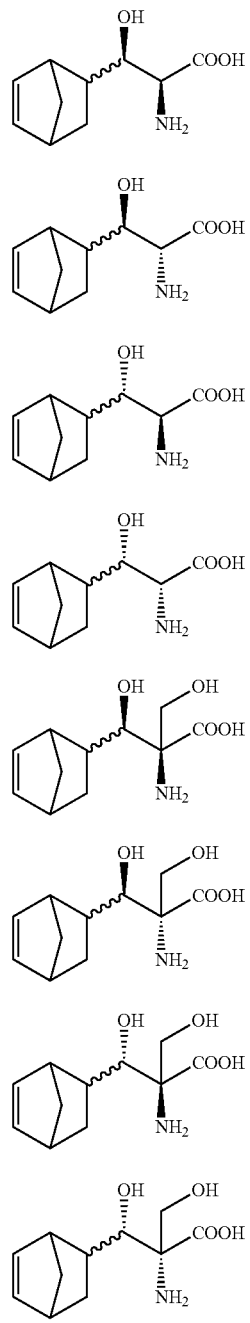

TABLE 1

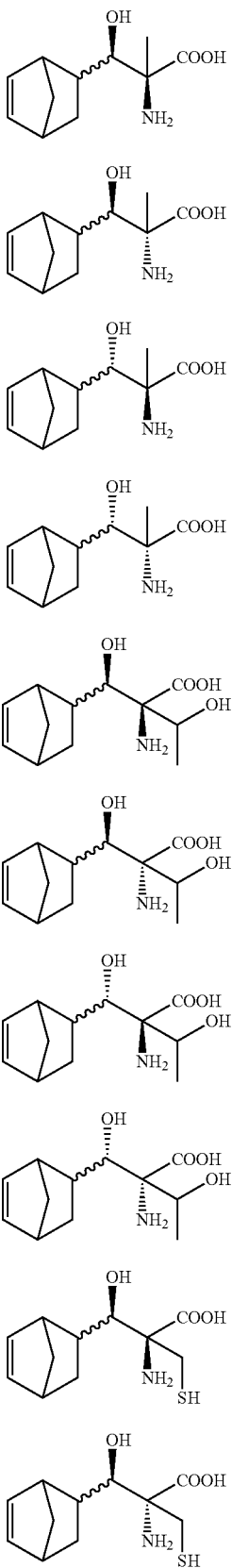

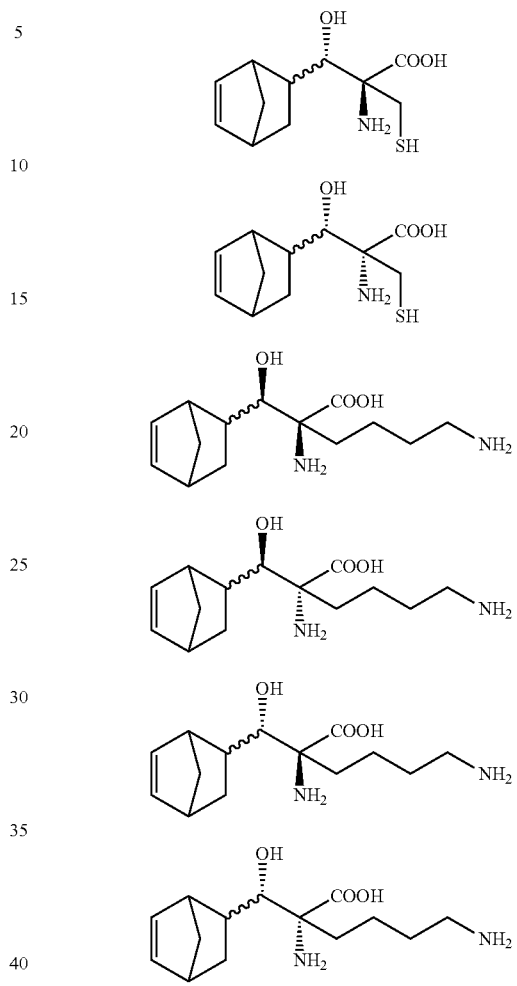

A further embodiment of the invention relates to a method for producing compounds as described herein. The method comprises the step of reacting norbornene-2-carboxaldehyde with an amino acid in the presence of threonine aldolase.

One embodiment of the invention relates to the method as described herein, wherein the amino acid is selected from the group consisting of glycine, alanine, serine, isoleucine, leucine, threonine, glutamic acid, proline, methionine, arginine, asparagine, glutamine, lysine and cysteine.

One embodiment of the invention relates to the method as described herein, wherein the threonine aldolase is of eukaryotic or prokaryotic origin, preferably of bacterial, yeast or fungal origin.

A further embodiment of the invention relates to the method as described herein, wherein the threonine aldolase is from *Pseudomonas, Sphingomonas, Azorhizobium, Methylobacterium, Escherichia, Thermotoga, Silicibacter, Paracoccus, Bordetella, Colwellia, Saccharomyces*, preferably from *Pseudomonas putida*.

A further embodiment of the invention relates to the method as described herein, wherein the threonine aldolase is comprised as cell lysate.

A further embodiment of the invention relates to a polypeptide comprising at least one amino acid of general formula I.

A further embodiment of the invention relates to a polypeptide as described herein, wherein said amino acid having a norbornene group is incorporated at a position corresponding to the amino acid residue in the wild type polypeptide.

One embodiment of the invention relates to a polypeptide as described herein, wherein said norbornene group is linked to a tetrazine or azide group.

One embodiment of the invention relates to a method of producing a polypeptide comprising a norbornene group, comprising providing a polypeptide as described herein, contacting said polypeptide with a tetrazine or azide compound, and incubating to allow linkage of the tetrazine or azide to the norbornene group via cycloaddition reaction.

One embodiment of the invention relates to a method of producing a polypeptide as described herein, wherein the compound of general formula I is genetically incorporated into a polypeptide or via peptide synthesis.

A further embodiment of the invention relates to the use of a compound of general formula I as building block in chemistry or as synthon for pharmaceutical ingredients.

DESCRIPTION OF EMBODIMENTS

Figure 1:
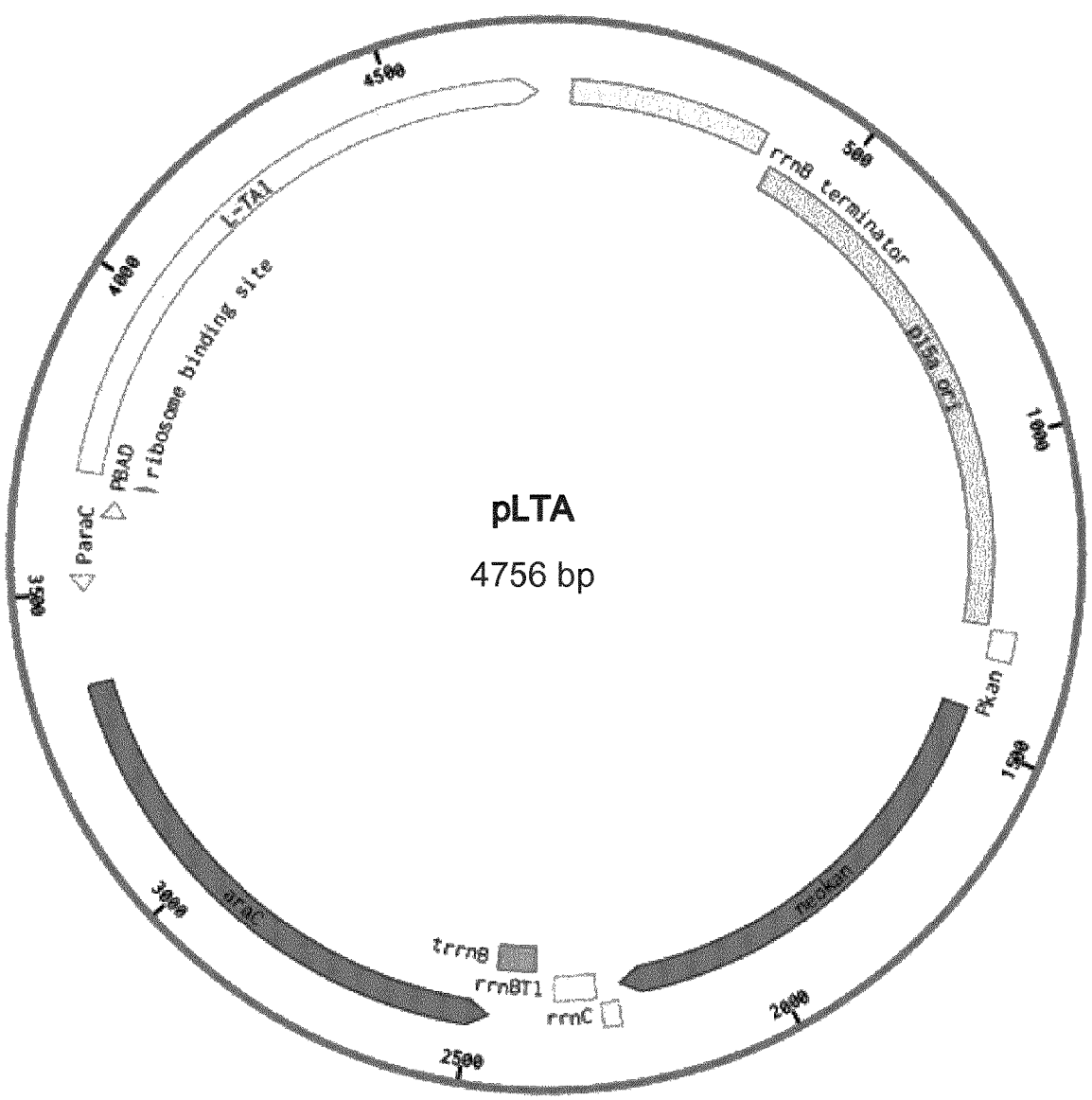
FIG. 1 depicts the expression vector. The gene for the threonine aldolase is under the control of an inducible arabinose promoter. The vector is maintained in the host cell by an p15a origin of replication. Resistance to kanamycin is conferred by the constitutive expression of the kan gene.

The present invention relates to novel β-hydroxy amino acids bearing a norbornene moiety at the beta carbon. This novel β-hydroxy amino acid compounds are able to react with various groups, e.g., tetrazines, azides, in click chemistry reactions at very fast rates at physiological pH in aqueous conditions at room temperatures.

Thus, one embodiment of the invention relates to novel β-hydroxy amino acid compounds of general formula I,

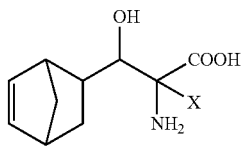

wherein X is H or —$C_1$-$C_6$alkyl, optionally substituted by hydroxy, halogen, amine, thiol, or carboxy.

The novel compounds are either provided by a synthetic route or by biocatalytic synthesis. L- and D-threonine aldolases have been employed in the synthesis of β-hydroxy-α-amino acid using benzaldehyde and glycine. However, aldolases are known to be flexible for the acceptor but rigid for the donor substrate. Although they accept glycine, they do not accept D- and L-alanine, DL-leucine, glycine ethylester, glycine amide and ethanolamine together with benzaldehyde or acetaldehyde (Steinreiber et al., 2007).

Surprisingly it was found by the inventor that L- and D-threonine aldolases accept D- and L-alanine, D- and L-serine, and D- and L-lysine as amino acid donors and norbornene-2-carboxaldehyde as aldehyde acceptor.

Thus, a further embodiment of the invention relates to a method for producing novel β-hydroxy amino acid compounds, wherein norbornene-2-carboxaldehyde is reacted with an amino acid in the presence of threonine aldolase.

The term "threonine aldolase" as used herein refers to an enzyme having threonine aldolase activity, which belong to the group of aldehyde dependent carbon carbon lyases (EC 4.1.2), and preferably belonging to the enzyme classification classes of EC 4.1.2.5 or EC 4.1.2.25. Threonine aldolase activity is defined as the ability to catalyze the reversible splitting of a β-hydroxy-α-amino acid into glycine and the corresponding aldehyde. Threonine aldolases are sometimes also referred to as phenylserine aldolases or β-hydroxy aspartate aldolases. Threonine aldolases are virtually ubiquitous enzymes and may for example be found in Bacteria, Archaea, yeasts and fungi including for example *Pseudomonas, Escherichia, Aeromonas, Thermotoga, Silicibacter, Paracoccus, Bordetella, Colwellia* and *Saccharomyces*. Specifically, the enzyme is form *P. putida, P. aeruginosa, P. fluorescence, E. coli, A. jandaei, T. maritima, Silicibacter pomeroyi, P. denitrificans, B. parapertussis, B. bronchiseptica, C. psychrerythreae,* and *S. cerevisiae*. Preferably, the threonine aldolase is from a *Pseudomonas* species, such as e.g. *P. putida, P. fluorescence* or *P. aeruginosa* is used. It is known to the person skilled in the art how to find threonine aldolases that are suitable for the conversion of amino acids and the specific norbornene-2-carboxaldehyde. Preferably, a threonine aldolase from *P. putida* is used.

The threonine aldolase employed in a method according to the invention may be a wild type enzyme or a genetically engineered enzyme.

For example, the threonine aldolase may be present, for example in the form of a dispersion, emulsion, a solution or in immobilized form, as crude enzyme, as a commercially available enzyme, as an enzyme further purified from a commercially available preparation. The threonine aldolase may be obtained from its source by a combination of known purification methods, in whole (optionally permeabilized and/or immobilized) cells that naturally or through genetic modification possess threonine aldolase, or in a lysate of cells with such activity. The expression of threonine aldolase in the whole cell may be enhanced using methods known to the skilled person. It will be clear to the skilled person that use can also be made of mutants of naturally occurring (wild type) enzymes with threonine aldolase in the process according to the invention. Mutants of wild-type enzymes can for example be made by modifying the DNA encoding the wild type enzymes using mutagenesis techniques such as for example random mutagenesis, site-directed mutagenesis, directed evolution, gene shuffling, fusion proteins, for example a fusion protein of threonine aldolase and decarboxylase; etc., so that the DNA encodes an enzyme that differs by at least one amino acid from the wild type enzyme and by effecting the expression of the thus modified DNA in a suitable (host) cell. Mutants of the threonine aldolase may have improved properties, for example with respect to selectivity for the substrate and/or activity and/or stability and/or solvent resistance and/or pH profile and/or temperature profile. Also, or alternatively, the DNA encoding the wild type enzyme may be modified in order to enhance the expression thereof.

It is understood that the term "enantioselective threonine aldolase" refers to an enzyme that prefers one of the enantiomers of the β-hydroxy-α-amino acid intermediate corresponding to the aldehyde used, i.e. a threonine aldolase that has enantioselectivity for either the L- or the D-configuration of the carbon on the α-position with respect to the carboxylic acid group (the carbon with an amino group attached). For example, threonine aldolases that are selective for the L-configuration of the α-carbon with respect to the carboxylic acid group as well as threonine aldolases that are selective for the D-configuration thereof are known to the skilled person.

The enantioselectivity of the threonine aldolase is at least 90%, preferably at least 95%, more preferably at least 98% or most particularly at least 99%.

As used herein the term with a 90% enantioselectivity is meant that the amino acid and the corresponding aldehyde are converted into 90% of one of the enantiomer of the β-hydroxy-α-amino acid intermediate and into 10% of the other enantiomer of the corresponding β-hydroxy-α-amino acid. The diastereomeric excess (d.e.) of the preferably formed stereoisomer will then be 80%.

The reaction conditions chosen depend on the choice of the enzyme. The skilled person knows how to optimize various parameters such as temperature, pH, concentration, use of solvent etc. The temperature and the pH are not very critical in the process of the invention. Preferably, however, the process is carried out at a pH between 4 and 10. In particular, the conversion is carried out at a pH between 4.5 and 8.0, or at a pH between 6.0 and 7.5. The temperature is preferably chosen between 0 and 80° C. Preferably, the temperature is between 5° C. and 50° C., or between 10° C. and 40° C., or between 25 and 37° C.

Suitable solvents for the process of the invention include for example water, one phase mixtures of water and a water miscible organic solvent, for example alcohols miscible with water, e.g., methanol, dimethylsulfoxide, dimethylformamide, N-methylpyrrolidone, acetonitrile; or two-phase mixtures of water and a non-miscible organic solvent, for example hydrocarbons, ethers etc., or so-called ionic liquids such as for example, 1,3-dialkyl imidazolium salts or N-alkyl pyridinium salts of acids like hexafluorophosphoric acid, tetrafluoroboric acid, or trifluoromethane sulphonic acid, or with $(CF_3SO_2)_2N^-$ as anionic counterpart. Preferably, in the process of the invention a one-phase mixture of water and dimethylsulfoxide (DMSO) is used, for example water with a DMSO content between 1 and 50% v/v, or between 5 and 30% v/v, or between 10 and 20% v/v.

Also, it is possible to perform the process of the present invention in an emulsion system, such as macro- or microemulsions, bi-continuous systems comprising an organic phase (with the norbornenecarboxaldehyde substrate), an aqueous phase (usually with the amino acid and the threonine aldolase) and a suitable surfactant (non-ionic, cationic or anionic), or the like.

The molar ratio between the amino acid or a salt thereof and the norbornene-carboxaldehyde is in principle not critical. The molar ratio between amino acid or a salt thereof and the norbornene-carboxaldehyde is >1 and may for example be 1000:1, or 100:1, or 10:1.

The order of addition of the reagents, amino acid or a salt thereof, the norbornene-carboxaldehyde; and the enzyme threonine aldolase is in principle not critical. For example, the process may be conducted in batch (i.e. everything added at once) or in a fed-batch mode (typically i.e. by feeding one or both reagents; however, enzyme(s) may also be fed). It may be of advantage to remove the β-hydroxy amino acid formed during the reaction and/or to recycle threonine aldolase. This can be done in batches, but may of course also be done continuously.

It may be of advantageous to add cofactors to the reaction to enhance the enzymatic activity of threonine aldolase. Examples of cofactors are known to the skilled person and include pyridoxal-5-phosphate, coenzyme B12, flavin adenine dinucleotide, phosphopantheine, thiamine, S-adenosylmethionine, biotin, salts, for example $Mg^{2+}$, $Mn^{2+}$, $Na^+$, $K^+$ and $Cl^-$. The selection of cofactor depends on the selection of enzyme, for example the enzymatic activity threonine aldolase from *P. putida* may be enhanced by addition of pyridoxal-5-phosphate. For example, pyridoxal-5-phosphate may be added to the process in a concentration between 0.001 and 10 mM, or between 0.01 and 1 mM, or between 0.1 and 0.5 mM.

Optimal amounts of the threonine aldolase depend on the substrate aldehyde used and can easily be determined by the skilled person through routine experimentation. The amino acid or a salt thereof may be used in a concentration between 0.1 and 4 M, or between 0.5 and 3 M, or between 1.0 and 2.5 M.

The norbornene-carboxaldehyde may be used in a concentration between 1 and 1000 mM, or between 10 and 500 mM, or between 20 and 100 mM.

A further embodiment of the invention relates to a polypeptide comprising a single amino acid having a norbornene group. Having only a single amino acid bearing a norbornene group provides a precisely defined polypeptide product. Having only a single amino acid bearing a norbornene group avoids problems of multiple labelling or incomplete labelling (if a reaction does not go to completion, heterogeneous products can result which can be a problem which is usefully addressed by having only a single amino acid bearing a norbornene group). In some embodiments said norbornene group is present as an amino acid residue of a norbornene glycine, norbornene alanine, norbornene serine, norbornene isoleucine, norbornene leucine, norbornene threonine, norbornene glutamic acid, norbornene proline, norbornene methionine, norbornene arginine, norbornene asparagine, norbornene glutamine, norbornene lysine and norbornene cysteine. Some embodiments of the invention relates to norbornene group present as an amino acid residue of a norbornene glycine, norbornene alanine, norbornene serine, or norbornene lysine. In preferred embodiments said single amino acid is not the N-terminal amino acid. Preferably the N-terminal amino group does not comprise norbornene. A further embodiment of the invention relates to a polypeptide wherein the amino acid residue bearing the norbornene is an internal amino acid of the polypeptide.

Some embodiments of the invention relate to methods of producing a polypeptide comprising a norbornene group, said methods comprising genetically incorporating an amino acid comprising a norbornene group into a polypeptide. Genetically incorporating the norbornene group allows precise construction of a defined polypeptide. The location of the norbornene group can be precisely controlled. This advantageously avoids the need to subject the whole polypeptide to complex reaction steps for addition of the norbornene group.

Suitably the method described for producing the polypeptide comprises
(i) providing a nucleic acid encoding the polypeptide which nucleic acid comprises an orthogonal codon encoding the amino acid having a norbornene group;
(ii) translating said nucleic acid in the presence of an orthogonal tRNA synthetase/tRNA pair capable of recognizing said orthogonal codon and incorporating said amino acid having a norbornene group into the polypeptide chain. Suitably said orthogonal codon comprises an amber codon (TAG), said tRNA comprises MbtRNAcuA and said tRNA synthetase comprises MbPylRS.

Suitably said amino acid comprising a norbornene group is a norbornene glycine, norbornene alanine, norbornene serine, norbornene isoleucine, norbornene leucine, norbornene threonine, norbornene glutamic acid, norbornene proline, norbornene methionine, norbornene arginine, norbornene asparagine, norbornene glutamine, norbornene lysine and norbornene cysteine. Some embodiments of the invention relates to norbornene group present as an amino acid residue of a norbornene glycine, norbornene alanine, norbornene serine, or a norbornene lysine.

Suitably said amino acids are listed above in Table 1.

In some embodiments the polypeptide comprises a single norbornene group. This has the advantage of maintaining specificity for any further chemical modifications which might be directed at the norbornene group. For example when there is only a single norbornene group in the polypeptide of interest then possible issues of partial modification (e.g., where only a subset of norbornene groups in the polypeptide are subsequently modified), or issues of reaction microenvironments varying between alternate norbornene groups in the same polypeptides (which could lead to unequal reactivity between different norbornene group(s) at different locations in the polypeptide) are advantageously avoided. Therefore, in some embodiments the polypeptide comprises a single norbornene amino acid residue.

A key advantage of incorporation of norbornene group is that is permits a range of extremely useful further compounds such as labels to be easily and specifically attached to the norbornene group.

A further embodiment of the invention relates to said norbornene group which is joined to a tetrazine or azide group. The tetrazine or azide group may further be joined to a fluorophore or to a PEG group or to a pharmaceutically active substance.

The fluorophore may be selected from the group consisting of fluorescein, tetramethyl rhodamine (TAMRA) or boron-dipyrromethene (BODIPY).

In another aspect, the invention relates to a method of producing a polypeptide comprising a norbornene group, said method comprising providing a polypeptide comprising a norbornene group as described above, contacting said polypeptide with a tetrazine or azide compound, and incubating the mixture to allow joining of the tetrazine or azide to the norbornene group by a cycloaddition reaction. Said cycloaddition reaction may be for example an inverse electron demand Diels-Alder cycloaddition reaction.

This chemistry has the advantage of speed of reaction. Thus suitably said reaction is allowed to proceed for 16 h, 14 h, 12 h, 10 h, 9 h, 8 h, 7 h, 6 h, 5 h, 4 h, 3 h, 2 h, or even less. In some embodiments of the invention said reaction is allowed to proceed for 30 min or even less.

In another aspect, the invention relates to a method of PEGylating a polypeptide comprising carrying out the method as described above wherein said tetrazine or azide compound is joined to a PEG group. It will be noted that certain reaction environments may affect reaction times. The shortest times such as 2 h, 30 min or less are applied to in vitro reactions.

Reactions in vivo, or in eukaryotic culture conditions such as tissue culture medium or other suitable media for eukaryotic cells, may need to be conducted for more than 30 min or longer than 2 hours to achieve the desired labelling.

Also described herein are methods of making polypeptides comprising a norbornene group, said method comprising modifying a nucleic acid encoding said polypeptide to provide an amber codon at one or more position(s) corresponding to the position(s) in said polypeptide where it is desired to incorporate a norbornene group. Suitably modifying said nucleic acid comprises mutating any codon to an amber codon (TAG).

Targeting (i.e. substitution with unnatural amino acid e.g. via amber suppression) is suitably done so that the chosen position is accessible to the tetrazine- or azide-fluorophore, i.e. lies on the surface of the folded protein. Thus polar amino acids in the original wildtype sequences are especially suitable positions to be targeted.

In principle the invention can be applied to any position in the polypeptide. Suitably the invention is not applied to the N-terminal amino acid of the polypeptide. When selecting the position of the amino acid to be targeted in the polypeptide of interest, it is advantageous to select a surface residue. Surface residues may be determined by sequence analysis, or by three dimensional molecular modelling. Surface residues may be determined by any suitable method known in the art. Advantages of targeting surface residues include better presentation of dyes such as fluorophores or labels such as biophysical labels. Advantages of targeting surface residues include simpler or more efficient downstream modifications. Advantages of targeting surface residues include less likelihood of disruption of polypeptide structure and/or function by application of the label.

Particularly suitable amino acid residues to target in the polypeptide of interest include non-hydrophobic residues. Suitably hydrophobic residues are not targeted according to the invention. Suitably hydrophilic residues are targeted. Suitably polar residues are targeted. Suitably glycine, alanine, serine, isoleucine, leucine, threonine, glutamic acid, proline, methionine, arginine, asparagine, glutamine, lysine, or cysteine are targeted. Suitably glycine, alanine, serine, or lysine are targeted. "Targeted" as used herein means substituting the codon for the residue being targeted for the orthogonal codon and synthesizing the polypeptide as described herein.

In another aspect, the invention relates to a homogenous recombinant polypeptide as described above. Suitably said polypeptide is made by a method as described above.

A further embodiment of the invention relates to a polypeptide produced according to the method(s) described herein. As well as being the product of those new methods, such a polypeptide has the advantageous technical feature of comprising a norbornene group.

Mutating has its normal meaning in the art and may refer to the substitution or truncation or deletion of the residue, motif or domain referred to. Mutation may be effected at the polypeptide level e.g., by synthesis of a polypeptide having the mutated sequence, or may be effected at the nucleotide level e.g., by making a nucleic acid encoding the mutated sequence, which nucleic acid may be subsequently translated to produce the mutated polypeptide. Where no amino acid is specified as the replacement amino acid for a given mutation site, suitably a randomization of said site may be used.

A fragment is at least 10 amino acids in length, or at least 25 amino acids, or at least 50 amino acids, or at least 100 amino acids, or at least 200 amino acids, or at least 250 amino acids, or at least 300 amino acids, or at least 313 amino acids, or the majority of the polypeptide of interest.

In the method according to the invention, said genetic incorporation preferably uses an orthogonal or expanded genetic code, in which one or more specific orthogonal codons have been allocated to encode the specific amino acid residue with the norbornene group so that it can be genetically incorporated by using an orthogonal tRNA synthetase/tRNA pair. The orthogonal tRNA synthetase/tRNA pair can in principle be any such pair capable of charging the tRNA with the amino acid comprising the norbornene group and capable of incorporating that amino acids comprising the norbornene group into the polypeptide chain in response to the orthogonal codon. The orthogonal codon may be the orthogonal codon amber, ochre, opal or a quadruplet codon or any other triplet codon. The codon simply has to correspond to the orthogonal tRNA which will be used to carry the amino acid comprising the norbornene group. Preferably the orthogonal codon is amber.

Polynucleotides encoding the polypeptide of interest for the method as described herein may be incorporated into a recombinant replicable vector. The vector may be used to replicate the nucleic acid in a compatible host cell. Thus in a further embodiment, the invention provides a method of making polynucleotides of the invention by introducing a polynucleotide according to the invention into a replicable vector, introducing the vector into a compatible host cell, and growing the host cell under conditions which allow replication of the vector. The vector may be recovered from the host cell. Suitable host cells include bacteria such as *E. coli* as well as yeasts such as *S. cerevisae* and *P. pastoris* as well as higher eukaryotic host cells like insect cells, HEK cells and Chinese Hamster Ovary cells.

Preferably, a polynucleotide of the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences. Vectors of the invention may be transformed or transfected into a suitable host cell as described to provide for expression of a protein of the invention. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid. Vectors may be used, for example, to transfect or transform a host cell.

Control sequences operably linked to sequences encoding the protein of the invention include promoters/enhancers and other expression regulation signals. These control sequences may be selected to be compatible with the host cell for which the expression vector is designed to be used in. The term promoter is well-known in the art and encompasses nucleic acid regions ranging in size and complexity from minimal promoters to promoters including upstream elements and enhancers.

Another aspect of the invention is a method, such as an in vivo method, of incorporating the norbornene containing amino acid(s) genetically and site-specifically into the protein of choice, suitably in a bacterial or eukaryotic cell. One advantage of incorporating genetically by said method is that it obviates the need to deliver the proteins comprising the norbornene amino acid into a cell once formed, since in this embodiment they may be synthesized directly in the target cell. The method comprises the following steps:

i) introducing, or replacing a specific codon with, an orthogonal codon such as an amber codon at the desired site in the nucleotide sequence encoding the protein ii) introducing an expression system of orthogonal tRNA synthetase/tRNA pair in the cell, such as a pyrollysyl-tRNA synthetase/tRNA pair iii) growing the cells in a medium with the norbornene containing amino acid according to the invention.

Step (i) entails or replacing a specific codon with an orthogonal codon such as an amber codon at the desired site in the genetic sequence of the protein. This can be achieved by simply introducing a construct, such as a plasmid, with the nucleotide sequence encoding the protein, wherein the site where the norbornene containing amino acid is desired to be introduced/replaced is altered to comprise an orthogonal codon such as an amber codon. This is well within the skilled person's ability and examples of such are given herein.

Step (ii) requires an orthogonal expression system to specifically incorporate the norbornene containing amino acid at the desired location (e.g., the amber codon). Thus a specific orthogonal tRNA synthetase such as an orthogonal pyrollysyl-tRNA synthetase and a specific corresponding orthogonal tRNA pair which are together capable of charging said tRNA with the norbornene containing amino acid are required. Examples of these are provided herein.

Host cells comprising polynucleotides according to the invention may be used to express proteins of the invention. Host cells may be cultured under suitable conditions which allow expression of the proteins of the invention. Expression of the proteins of the invention may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Proteins of the invention can be extracted from host cells by a variety of techniques known in the art, including enzymatic, chemical and/or osmotic lysis and physical disruption.

Proteins of the invention can be purified by standard techniques known in the art such as preparative chromatography, affinity purification or any other suitable technique.

Suitably the norbornene group incorporated into the polypeptide of interest is reacted with a tetrazine or azide compound. The tetrazine or azide acts to conveniently attach a molecule of interest to the polypeptide via the norbornene. Thus, the tetrazine or azide compound may already bear the molecule of interest.

Suitably said tetrazine or azide group may be further joined to any suitable molecule of interest for attaching same to the polypeptide via the norbornene-tetrazine or the norbornene-azide reaction.

Tetrazines are designed and synthesized in a way that they have a readily accessible primary amino group. This amino group can be reacted with a variety of compounds using standard amine coupling reactions. As tetrazines are stable in a wide variety of reaction conditions almost any compound can be coupled to the tetrazine of interest. Exemplary compounds joined to tetrazines (for attachment to polypeptide via the norbornene) include various fluorophores as mentioned herein. Tetrazines may also be coupled to more sophisticated fluorophores, e.g. those suitable for Super Resolution Microscopy, such as STORM, PALM or STED, (for example Alexa dyes or special dyes from Abberior, developed for STED microscopy). Lipids may be coupled to tetrazines via standard techniques. PEGs may be coupled to tetrazines (see examples), which are beneficial for PEGylation of polypeptides via the norbornene according to the invention. In all cases the key benefits of our approach include the fact that the incorporation of norbornene according to the invention is site specific and most importantly can be done in vivo (and/or in vitro in an organism such as *E. coli*). By contrast, in prior art approaches the purified antibody or protein can only be reacted in vitro with norbornene in a non-selective and not site-specific manner which has numerous problems as set out above. Thus the invention provides significant benefits compared to prior art methods as demonstrated herein.

The norbornene containing polypeptide of the invention may be conveniently conjugated to other biophysical labels than fluorophores, for example, NMR probes, Spin label probes, IR labels, EM-probes as well as small molecules, oligonucleotides, lipids, nanoparticles, quantum dots, biophysical probes (EPR labels, NMR labels, IR labels), small molecules (biotin, drugs, lipids), oligonucleotides (DNA, RNA, LNA, PNA), particles (nanoparticles, viruses), polymers (PEG, PVC), proteins, peptides, surfaces and the like.

The novel amino acids bearing norbornene are specifically useful for incorporation into polypeptides or proteins. Thus conjugation of the polypeptide or protein to moieties bearing a tetrazine or azide moiety is envisaged. The modified polypeptides or proteins may be used as active pharmaceutical ingredients. The novel amino acid compounds having the norbornene moiety may be incredibly useful as building blocks in peptide chemistry and as novel synthons for pharmaceutical ingredients.

The compounds are specifically useful as a building block for the chemical or enzymatic synthesis of polypeptides, proteins, or analogues or precursors thereof. It is understood that the term "building block" refers to structural units which are used in chemical or enzymatic operations.

In the context of the present invention, the term "synthon" refers to a compound that is, or can be used as, a synthetic equivalent for a particular compound of interest in a chemical reaction, e.g. in the synthesis of an active pharmaceutical ingredient.

EXAMPLES

The Examples which follow are set forth to aid in the understanding of the invention but are not intended to, and should not be construed to limit the scope of the invention in any way. The Examples do not include detailed descriptions of conventional methods. Such methods are well known to those of ordinary skill in the art.

Methods:

*E. coli* cells harboring the gene for phenyl serine/threonine aldolase are cultured and express phenyl serine/threonine aldolase. After harvesting, the cells are disrupted using standard cell disruption procedures. The cell debris is removed by centrifugation to give clear cell lysate. The lysate is buffered using 50 mM phosphate buffer to a pH in the range of 6-9. The amino acid and the aldehyde (dissolved in 20% total volume of an organic co-solvent (DMSO)) are then added to the lysate and reacted at 30° C. for 24 h. The product precipitates during the course of the reaction and is recovered by pH adjustment and centrifugation.

Protein Incorporation:

A mutant pyrrolysyl-tRNA synthetase, obtained from a wild-type pyrrolysyl-tRNA synthetase, which is Methanosarcina-derived pyrrolysyl-tRNA synthetase, and/or the mutant pyrrolysyl-tRNA synthetase aminoacylates a pyrrolysine tRNA, incorporates amino acids as described herein.

Plasmid Creation:

The gene for phenylserine/threonine aldolase was amplified using *Pseudomonas putida* kt2440 (DSM-6125) genomic DNA as template. The template was prepared by simple cell lysis with concomitant DNA precipitation using ethanol. The primers used are shown below:

```
LTA Fwd:
GCTAATTCATATGACAGACAAGAGCCAACAATTCGCCAGC

LTA Rev:
TACGATTAAGCTTTTATTAGCCACCAATGATCGTGCGGATATC
```

The enzyme was cloned into a low-copy vector using restriction enzymes (NdeI, HindIII) to be under the control of an L-arabinose inducible expression system.

Enzyme Expression:

The plasmid containing L-TA1 was transformed into *E. coli* BL21(DE3) and positive clones were selected by plating on a LB plate containing 50 µg/mL kanamycin. A single colony was picked and inoculated into 15 mL sterile LB medium containing kanamycin. The culture was incubated at 37° C. under shaking overnight. The next day 1 L of Terrific Broth medium containing 50 mM glucose and 50 µg/mL kanamycin was inoculated with the 15 mL overnight culture. The culture was grown under shaking at 37° C. for 4 h when expression of the enzyme was induced by adding 0.2% L-arabinose. After induction, the culture was transferred to shaking at 30° C. and incubated overnight. The next day the culture was harvested by spinning down at 5,000 g for 30 min at 4° C. The cell pellet was washed with 0.9% sterile NaCl and again pelleted under the same conditions. The cell pellets were frozen at −20° C. until further use.

Amino Acid Synthesis:

Cell pellets from 500 mL culture were thawed at room temperature and resuspended in 30 mL 50 mM $Na_2HPO_4$ buffer pH 8. The cell suspension was lysed using sonication. Cell debris was pelleted at 15,000 g for 30 min at 4° C. For amino acid synthesis, the lysate is mixed 1:7 with a 100 mM $Na_2HPO_4$ buffer pH 7 that contains 1 M of the respective amino acid, 20% DMSO and 300 mM of norbornene carboxaldehyde. The reaction mixture is incubated for 16 hours at 30° C. The resulting white precipitate is harvested by centrifugation at 8,000 g for 30 min and dried by lyophilisation to obtain the amino acid.

The norbornene bearing amino acid is incorporated for example into human growth hormone, parathyroid hormone, or fluorescent proteins.

Co-Solvent Screening:

Cell lysate was prepared as described above. The co-solvent screening was performed in 1.5 mL Eppendorf tubes. The components were added in the following order: 50 mM $Na_2HPO_4$ buffer (pH 8.0), co-solvent, aldehyde and the lysate. The composition of the reaction mixture is summarized in Table 1. 10% & 20% (v/v) of following co-solvents were tested: acetone, acetonitrile, butane-1-ol, tert-butanol, 1,4-dioxane, DMSO, ethanol, ethyl acetate, ethylene glycol, glycerol, THF and toluene.

TABLE 2

Composition of reaction mixture for co-solvent screening

| | amount [μL] | | | |
|---|---|---|---|---|
| | norbornene carboxaldehyde | buffer B | co-solvent | lysate |
| 10% co-solvent | 35 | 845 | 80 | 35 |
| 20% co-solvent | 35 | 765 | 160 | 35 |

The product precipitate was spun down at 13,000 rpm for 10 minutes. Then the supernatant was decanted and the Eppis again spun at 13,000 rpm for 10 min. Residual supernatant was pipetted off. Pellets were freeze dried. To this end, the lyophilisator was pre-cooled to −53° C. and the samples frozen at −20° C. The samples were then placed in the vacuum for 2 hrs. After this, the rack temperature was increased to 40° C. and drying commenced for 20 hours. The yield clearly depended on the co-solvent used (see FIG. 1).

The stereochemical distribution of the products formed can be controlled by the enzyme, as well as the co-solvent used. In case of tert-butanol the main species obtained by HPLC-UV/HPLC-MS analysis (OPA/N-acetyl-L-cysteine (NAC) pre-column derivatization) revealed a stereochemical distribution of 85% for the main species.

Incorporation of the Norbornene Amino Acid into Green Fluorescent Protein Reporter A mutant pyrrolysyl-tRNA synthetase, obtained from a wild-type pyrrolysyl-tRNA synthetase, which is an archaeal-derived pyrrolysyl-tRNA synthetase (such as *Methanosarcina* or *Methanocaldococcus* or other), and/or the mutant pyrrolysyl-tRNA synthetase aminoacylates a pyrrolysine tRNA, incorporates amino acids as described herein. The mutant pyrrolysyl-tRNA synthetase was generated by state of the art protein engineering technologies, such as structure guided site-saturation mutagenesis or directed evolution or a combination. Also, other technologies such as gene shuffling would be possible.

The mutant pyrrolysyl-tRNA synthetase and the corresponding amber suppressor pyrrolysine tRNA were introduced into an expression vector harboring a p15a origin of replication, a variant of the green fluorescent protein reporter carrying an in frame amber stop codon at amino acid position 39 [Y39X], as well as an N-terminal hexahistidine tag and a kanamycin resistance gene. The mutant pyrrolysyl-tRNA synthetase was expressed from an arabinose inducible promoter and the suppressor pyrrolysine tRNA from a constitutive promoter commonly used for this purpose.

*E. coli* cells harboring the above described expression vector were cultivated in 250 mL flasks each containing 50 mL M9 minimal medium with 50 μg/mL kanamycin (Roth) and 1-2% glucose as C-source. Cultures were incubated at 37° C. on an orbital shaker at 160-180 rpm. At D600 of 0.8-1.0, the expression of the PylRS was induced by adding 0.2% (w/v) of arabinose (Roth). In addition, 5-10 mM of NorI dissolved in 1 M NaOH. Expression was carried out between 4-24 hours (temperature can be adjusted depending on the target enzyme; 37° C. for eGFP). Cells were harvested by centrifugation (5,000 g for 30 minutes at 4° C.). The eGFP variant was purified by Ni2+-affinity chromatography using Ni-NTA agarose following the instructions of the manufacturer.

Figure 2:
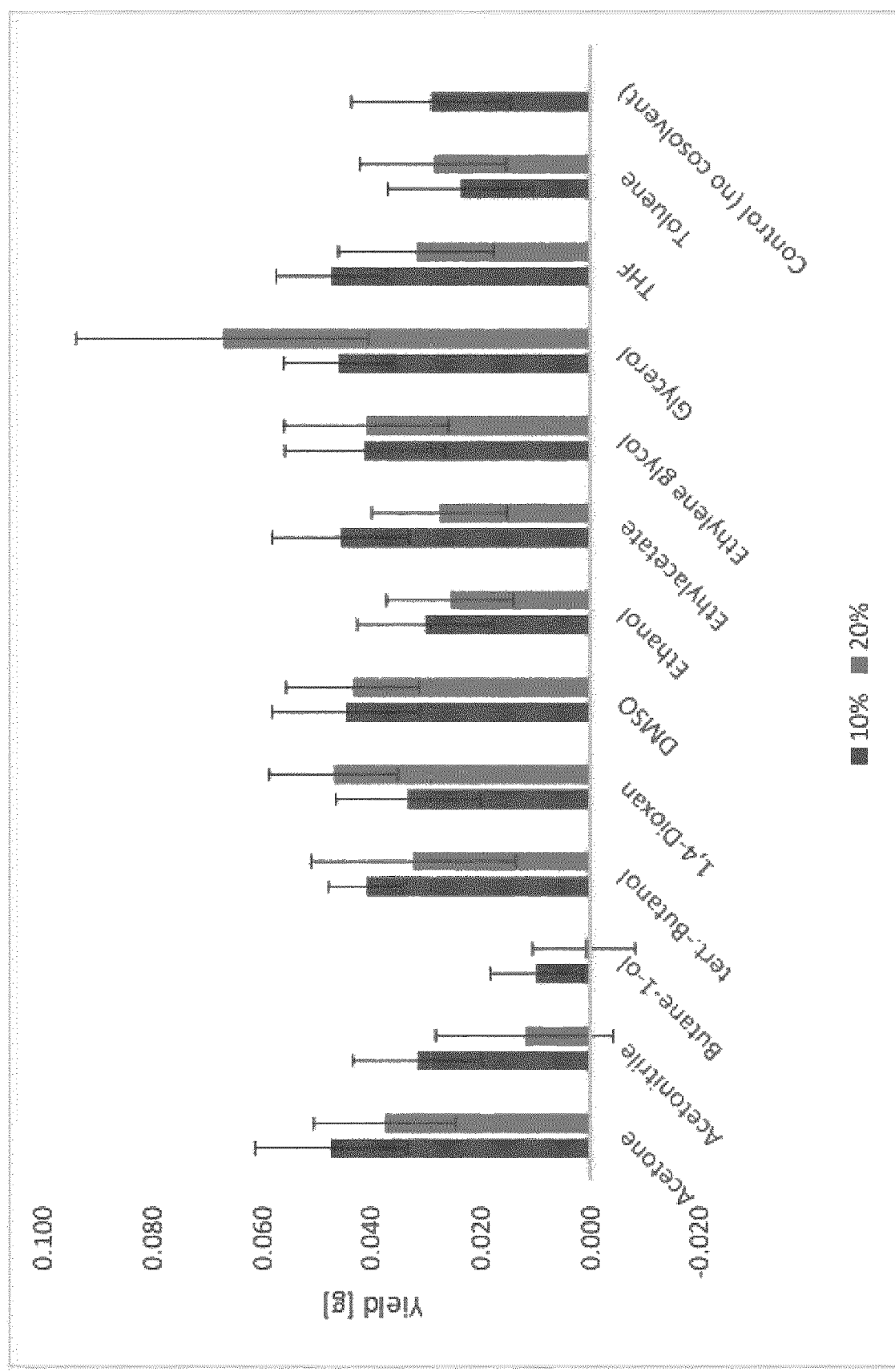
FIG. 2 shows the results of the co-solvent screening experiment.
Figure 3:
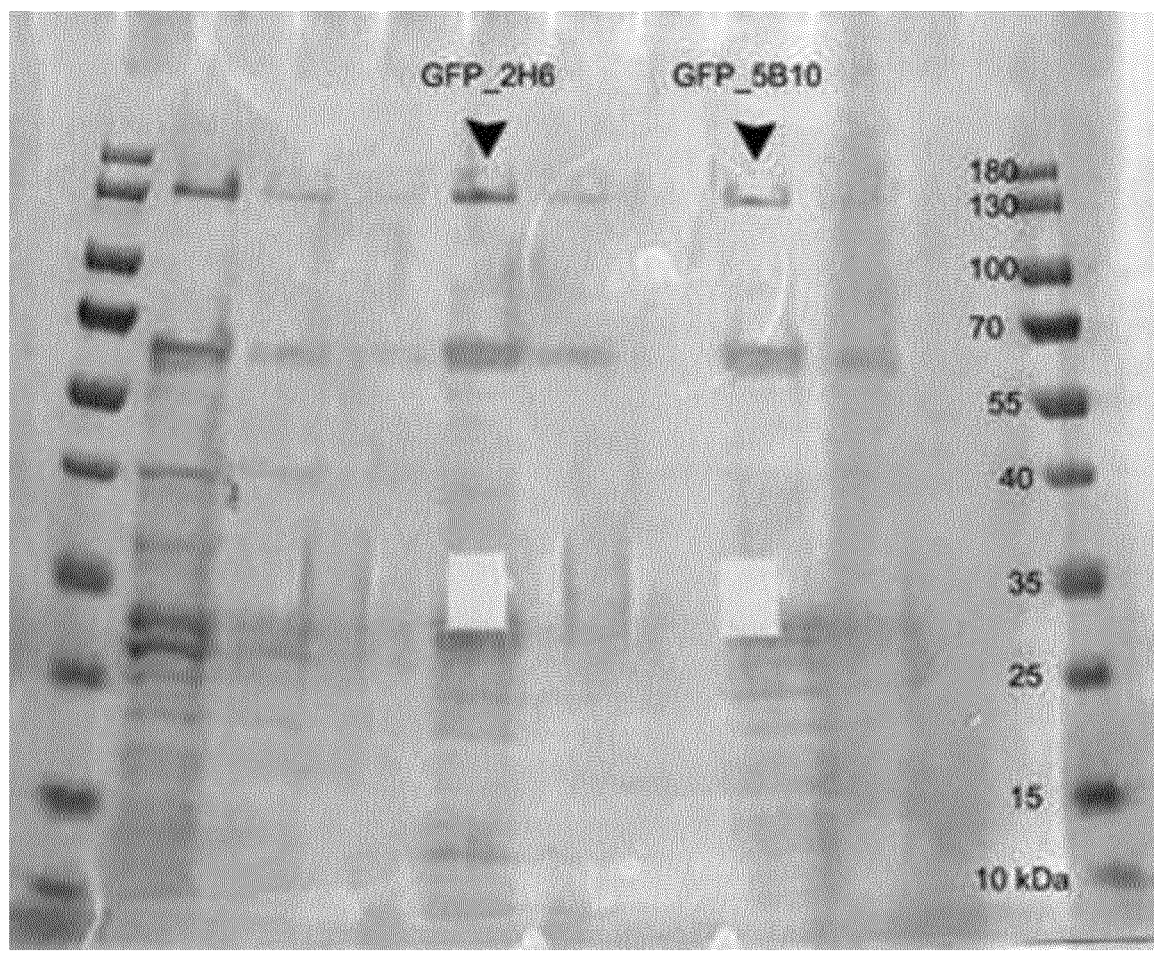
FIG. 3 shows an eGFP variant carrying NorI modified with tetrazine TAMRA excised for by peptide sequencing by tandem mass spectrometry.

Purified eGFP variant carrying the NorI was modified by conjugation chemistry applying a tetrazine bearing fluorescent dye as reaction partner, such as 6-Methyl-Tetrazine-5-TAMRA. Reactions were performed in 100 mM MES Buffer pH 6 and incubated between 4-24 hours. TAMRA labeled eGFP samples were separated on pre-casted SDS gel following the instructions of the manufacturer. The gels were exposed to UV-light to detect TAMRA fluorescence and subsequently stained with Coomassie Blue following standard procedures. The band at the expected size of eGFP (~28 kDa, see FIG. 2) was excised.

The presence of the NorI compound, as well as the TAMRA modification was confirmed by peptide sequencing by tandem mass spectrometry. The successful TAMRA modification was also confirmed by obtaining a signal for TAMRA fluorescence at the size of eGFP.

The invention claimed is:

1. A compound having a norbornene group which has the following formula I:

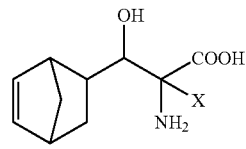

wherein X is H or $C_1$-$C_6$ alkyl, optionally substituted with a hydroxy, halogen, amine, thiol, or carboxy moiety, or wherein the compound is selected from the group consisting of D- or L-2-methylpyrrolidine-3-norbornene serine, D- or L-2-methyl(propyl)sulfane-3-norbornene serine, D- or L-2-1-butylguanidine-3-norbornene serine, L-2-propionamide-3-norbornene serine, and L-2-butyramide-3-norbornene serine.

2. The compound of claim 1, wherein the compound is selected from the group consisting of D- or L-3-norbornene serine, D- or L-2-methyl alcohol-3-norbornene serine, D- or L-2-methyl-3-norbornene serine, D- or L-2-isopropyl alcohol-3-norbornene serine, D- or L-2-methyl thiol-3-norbornene serine, D- or L-2-butane amine-3-norbornene serine, D- or L-2-isopentane-3-norbornene serine, D- or L-2-butyric acid-3-norbornene serine, D- or L-2-methylpyrrolidine-3-norbornene serine, D- or L-2-methyl(propyl)sulfane-3-norbornene serine, D- or L-2-1-butylguanidine-3-norbornene serine, L-2-propionamide-3-norbornene serine, and L-2-butyramide-3-norbornene serine.

3. The compound of claim 1, wherein the compound is selected from the group consisting of compounds having the following chemical structures:

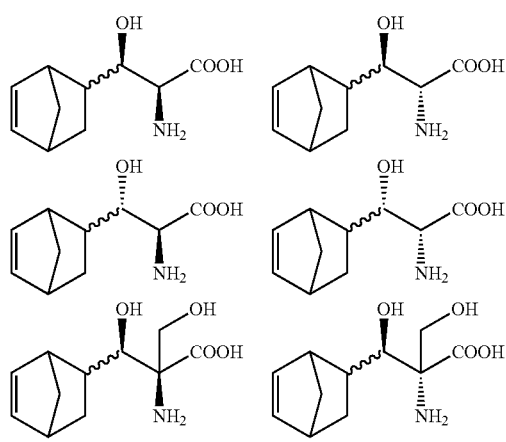

-continued

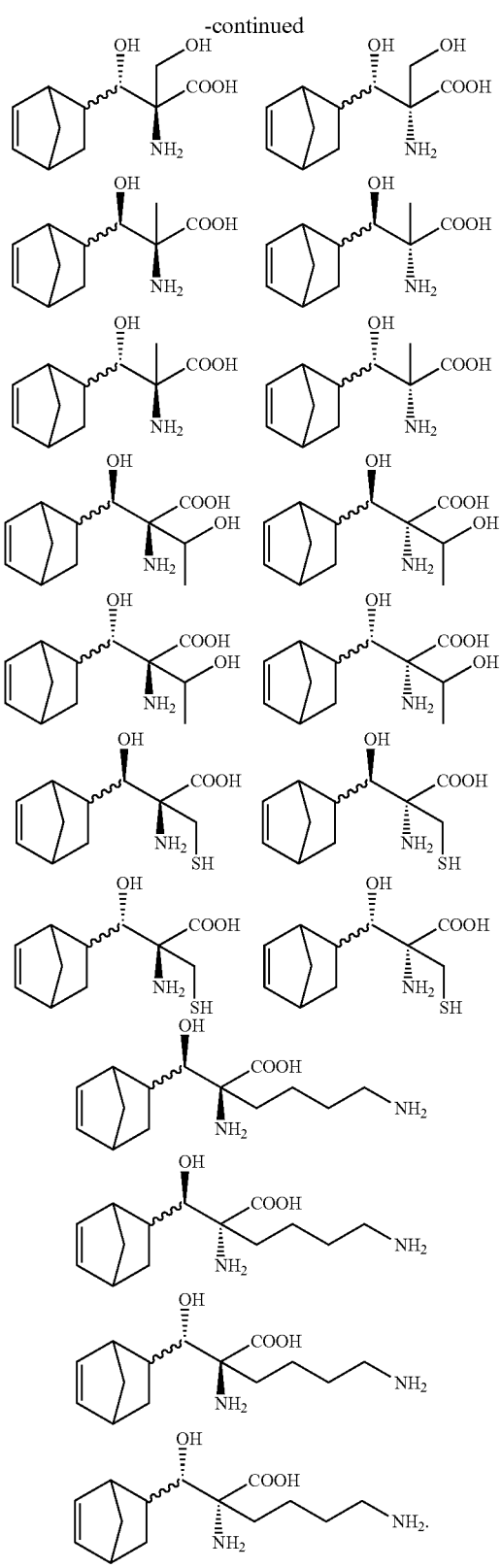

4. A method for producing compounds of formula I, comprising the step of reacting norbornene-2-carboxaldehyde with an amino acid in the presence of threonine aldolase.

5. The method according to claim 4, wherein the amino acid is selected from the group consisting of glycine, alanine, serine, isoleucine, leucine, threonine, glutamic acid, proline, methionine, arginine, asparagine, glutamine, lysine and cysteine.

6. The method according to claim 4 or 5, wherein the threonine aldolase is of eukaryotic or prokaryotic origin.

7. The method of claim 6, wherein the threonine aldolase is of bacterial, yeast or fungal origin.

8. The method according to claim 6, wherein the threonine aldolase is from an organism in a genus selected from the group consisting of *Pseudomonas, Sphingomonas, Azorhizobium, Methylobacterium, Escherichia, Thermotoga, Silicibacter, Paracoccus, Bordetella, Colwellia*, and *Saccharomyces*.

9. The method according to claim 8, wherein the threonine aldolase is from *Pseudomonas putida*.

10. The method according to claim 4, wherein the threonine aldolase is present in a cell lysate.

11. A polypeptide having a norbornene group which has the following formula II,

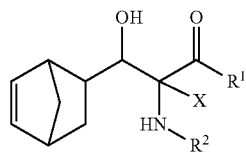

wherein:

X is H or $C_1$-$C_6$alkyl, optionally substituted with a hydroxy, halogen, amine, thiol, or carboxy moiety, $R^1$ is OH, an amino acid, or a polypeptide moiety, $R^2$ is H, an amino acid, or a polypeptide moiety, and at least one of $R^1$ and $R^2$ is an amino acid or a polypeptide moiety.

12. The polypeptide of claim 11, wherein the norbornene group is incorporated into the polypeptide at a position corresponding to the position of the corresponding amino acid residue lacking a norbornene group in a wild type form of the polypeptide.

13. The polypeptide of claim 11, wherein said norbornene group is linked to a tetrazine group.

14. A method of producing a polypeptide comprising a norbornene group, comprising providing a polypeptide which comprises the compound of claim 1, contacting said polypeptide with a tetrazine or azide compound, and incubating the polypeptide and the tetrazine or azide compound to allow linkage of the tetrazine or azide to the norbornene group via cycloaddition reaction.

* * * * *